United States Patent [19]

Brown et al.

[11] 4,137,332
[45] Jan. 30, 1979

[54] 1-(ALKOXYPHENYL)-5-(PHENYL)BIGUA-NIDE COMPOSITIONS FOR USE AS AGRICULTURAL FUNGICIDES

[75] Inventors: Michael J. Brown, Randolph; Bruce M. Resnick, West Paterson; James H. R. Woodland, Bloomingdale, all of N.J.

[73] Assignee: GAF Corporation, New York, N.Y.

[21] Appl. No.: 901,720

[22] Filed: May 1, 1978

[51] Int. Cl.$^2$ .............................................. A01N 9/20
[52] U.S. Cl. .................................................... 424/326
[58] Field of Search .......................... 424/326; 260/565

[56] References Cited

U.S. PATENT DOCUMENTS

| | | | |
|---|---|---|---|
| 2,704,710 | 3/1955 | Sprung | 260/565 |
| 3,222,398 | 12/1965 | Brown | 424/326 |

FOREIGN PATENT DOCUMENTS 4819934 6/1973 Japan ........................................ 424/326

OTHER PUBLICATIONS

Derwent Japanese Patents Report, 6, No. 29, pp. 5:1–5:2 (8-1967).

Primary Examiner—Albert T. Meyers
Assistant Examiner—H. Steven Seifert
Attorney, Agent, or Firm—W. C. Kehm; Walter Katz

[57] ABSTRACT

The present invention provides novel fungicidal compositions for agricultural use which comprise an effective amount of a 1-(alkoxyphenyl)-5-(phenyl)biguanide compound having the formula:

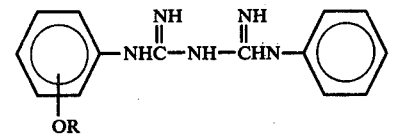

where R is alkyl, linear or branched, having from 1-14 carbon atoms; and also acid addition salts thereof, in a suitable inert carrier material.

The invention further relates to a method for controlling or protecting pathogenic fungi with a fungicidally effective amount of said compound. Fruit trees, especially apple trees, are controlled against the fungi which causes apple scab.

7 Claims, No Drawings

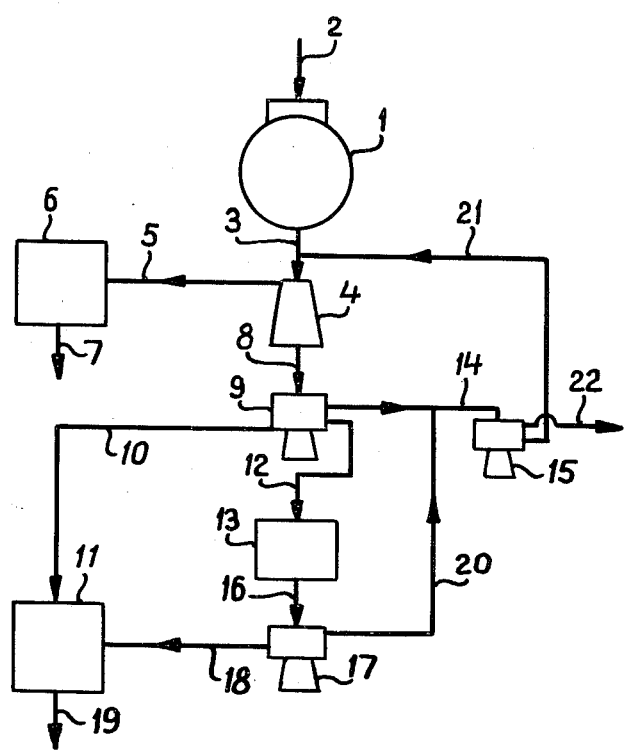

1-(ALKOXYPHENYL)-5-(PHENYL)BIGUANIDE COMPOSITIONS FOR USE AS AGRICULTURAL FUNGICIDES

BACKGROUND OF THE DISCLOSURE

1. Field of the Invention

This invention relates to 1-(alkoxyphenyl)-5-(phenyl)biguanide compositions for use as agricultural fungicides.

2. Description of the Prior Art

U.S. Pat. No. 2,704,710 discloses an alkoxydiphenyl biguanide compound to render azo dyes in color photographic emulsions fast to diffusion. However, no use is disclosed with respect to agricultural fungicidal activity for such compound.

U.S. Pat. No. 3,222,398 describes alkoxy substituted monophenylbiguanides as having mycobaceteriostatic activity including bacteriostatic and fungistatic activity, against skin and spoilage fungi, but no use as agricultural fungicides is mentioned or suggested.

SUMMARY OF THE INVENTION

The present invention provides novel fungicidal compositions for agricultural use which comprise an effective amount of a 1-(alkoxyphenyl)-5-(phenyl)biguanide compound having the formula:

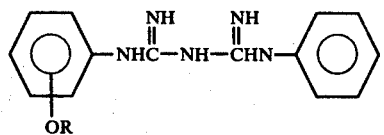

where R is alkyl, linear or branched, having from 1–14 carbon atoms; and also acid addition salts thereof, in a suitable inert carrier material.

Preferably, R is linear alkyl group having from 7–12 carbon atoms, and most preferably, R is $C_8$, and in which the alkoxy group is substituted in the para position. The preferred compound is 1-(p-n-octaoxyphenyl)-5-phenyl biguanide.

The invention further relates to a method for controlling pathogenic fungi with a fungicidally effective amount of Formula (I). Still further, the invention relates to a method for protecting living plants from attack by pathogenic fungi through the application to the foilage of said plants of a fungicidally effective amount of a Formula (I) compound.

In the preferred use of the invention, fruit trees, especially apple trees, are controlled against the fungi which causes apple scab, including both protective activity for healthy plants, and eradicative activity against the fungi present on the apple fruit itself.

The fungicidal compositions of the invention are applied as a formulation contaning a fungicidally effective amount of the active ingredient in an inert carrier. The formulation may take the form of a solution, a suspension, emulsion, wettable powder or dust for treating the foilage of the plants, or the fruit itself, or for addition to the soil. Preferably the compositions are applied as a spray of a liquid formulation.

DESCRIPTION OF THE PREFERRED EMBODIMENTS

The 1-(alkoxyphenyl)-5-(phenyl)biguanide compounds of the invention may be prepared by the method described in U.S. Pat. No. 2,704,710. In this procedure, alkoxy substituted aniline salts may be reacted with phenyldicyandiamide in a solvent to form the desired 1-(alkoxyphenyl)-5-(phenyl)biguanide compounds. Phenyldicyandiamide may be prepared by reacting sodium dicyanamide with aniline hydrochloride in a suitable solvent, as described in J. Am. Chem. Soc. 25,719 (1903). The alkoxy aniline starting materials generally are available commercially; otherwise, they may be prepared from o-, m- or p-hydroxyacetanilide by alkoxylation with the appropriate alkyl halide in basic solution, Ber. 3, 780 (1870).

Although the compounds herein may be employed as the free base, the acid addition salt thereof also may be used. For example, such salts as the halides, e.g. chloride, bromide or iodide; acetate, sulfate, hydrogen sulfate, methyl sulfate, benzene sulfonate, p-toluene sulfonate, nitrate and phosphate, are suitable acid addition salts.

Suitable inert carriers for use in the compositions of the invention include liquid or solid carriers. Suitable liquid carriers include water, acetone, dimethylsulfoxide, alcohols, such as methanol, propylene glycol, and diethylene glycol; N-methylpyrrolidone, isoparaffinic hydrocarbons, such as naphtha or kerosene; ethyl ether, formamide, methylformamide, and mixtures thereof, although many other available solvents may be used as well. Solid carriers or powder diluents may be used when the composition is applied as a dust.

It has been found that the compounds of this invention are useful for the control of fungi which infect many living plants; however, by way of example only, they may be used for controlling such common agricultural fungi such as rust and rice spot. However, they are particularly effective and useful for controlling fungi which are the causative agents for apple scab, and may be utilized in the protective or eradicative modes for this fungus.

As mentioned, in utilizing the above-identified 1-(alkoxyphenyl)-5-(phenyl)biguanide compounds for controlling pathogenic fungi with a fungicidally effective amount of a Formula (I) compound, it has been found most advantageous to apply the active material as a composition which includes an inert carrier. Preferably, it is applied as a liquid spray, in the form of a solution, suspension, or emulsion containing the active ingredient in a concentration from about 20–5,600 ppm. A concentration of about 50 to 500 ppm of the 1-(alkoxyphenyl)-5-(phenyl)biguanide compound is a particularly useful concentration for this purpose.

The fungicidal compositions may be prepared as a liquid formulation suitable for spraying. To form such a composition, the active compound first is added to a blend of a dispersant and a surfactant dissolved in a suitable solvent to form a liquid concentrate. Then the concentrate is diluted with water to provide the desired concentration of the active ingredient of the composition for spraying in the field. In a typical preparation of such a spray formulation, the concentrate containing the active ingredient in an amount of about 10%, and the surfactant-dispersant of about 8%, by weight, in acetone as a solvent, is diluted with water to the aforementioned 20–5,600 ppm concentration range.

Alternatively, a wettable powder emulsion may be prepared for spraying to the foliage or to the soil. The wettable powder may be made by admixing the active ingredient, for example, bentonite, chalk, clay, diatomaceous earth, fuller's earth, mica, silica, talc, ground slate, or any of the other usual extenders for agricultural chemicals, and incorporating wetting agents, and/or dispersing agents in such mixtures. The wettable powder then is diluted with water to form a liquid emulsion suitable for spraying.

The surfactants and other wetting agents, and dispersants, which may be included in the spray composition, insure complete contact with the fungus. Conventional nonionic surfactants which provide good wetting of the spray solution on the plant foliage include alkyl polyoxyethylene ethers, polyoxyethylene (20) sorbitan monolaurate, polyoxyethylene (20) sorbitan monoleate, alkylarylpolyglycol ethers, alkyl phenol ethoxylates, trimethyl nonyl polyethylene glycol ethers, alkyl phenol ethylene oxide condensates, octyl phenoxy polyethoxy ethanols, nonylphenyl polyethylene glycol ethers, condensates of polyoxy ethylenes, polyoxy propylenes, aliphatic polyethers, aliphatic polyesters, alkylaryl polyoxyethylene glycols, and the like.

Suitable dispersing agents include the calcium salt of a polymerized alkyl aryl sulfonic acid, sodium lignosulfonate, or sodium salt of condensed naphthalene sulfonic acid. About 1% to 5%, by weight, of a surfactant, such as polyoxyethylated vegetable oil, alkyl phenoxy polyoxyethylene ethanol, sodium alkyl naphthalene sulfonate often may also be blended with the dispersant formulation.

A typical emulsifier blend of surfactant and dispersing agent is Atlox 3404F, made by ICI America, which is a blend of a calcium sulfonate dispersant and a nonionic surfactant.

Alternatively, the compositions of the invention may be applied as a dust of particulate matter comprising the active ingredient in a solid powder, such as one or more of the above-mentioned extender diluents.

The fungicidal compositions of the invention generally are applied at a selected rate, preferably until the plants are drenched with the liquid spray, in an amount which will depend upon various circumstances including the susceptibility of the plants to the fungus, the weather, the stage of growth and various other factors.

The present invention herein is further illustrated by the following examples, which are not to be taken as limiting of the invention.

EXAMPLE 1

1-(p-n-OCTAOXYPHENYL)-5-(PHENYL)BIGUANIDE

A mixture of p-n-octaoxyaniline hydrochloride (12.0g.) and phenyldicyanidiamide (9.3g.) is reacted in ethanol (150 ml.) under reflux conditions for 16 hours. The reaction mixture then is poured into 2 l. of water containing 5 ml. of acetic acid. The product is purified by boiling in charcoal, and filtering. The desired compound is obtained by rendering the filtrate basic with aqueous alkali and filtering. The product is washed with water and dried to provide a yield of 16.8 g. (85%), m.p. 116° C.

EXAMPLE 2

Following the procedure of Example 1, using the alkoxyaniline starting materials listed below, and phenyldicyandiamide, there is produced also the corresponding 1-(alkoxyphenyl)-5-(phenyl)biguanide compounds.

| ALKOXYANILINE | 1-(ALKOXYPHENYL)-5-(PHENYL)BIGUANIDE |
|---|---|
| p-methoxyaniline* | 1-(p-methoxyphenyl)-5-(phenyl)biguanide |
| p-ethoxyaniline* | 1-(p-ethoxyphenyl)-5-(phenyl)biguanide |
| m-n-propoxyaniline | 1-(m-n-propoxyphenyl)-5-(phenyl)biguanide |
| p-n-butoxyaniline* | 1-(p-n-butoxyphenyl)-5-(phenyl)biguanide |
| p-n-pentoxyaniline* | 1-(p-n-pentoxyphenyl)-5-(phenyl)biguanide |
| p-n-hexaoxyaniline* | 1-(p-n-hexaoxyphenyl)-5-(phenyl)biguanide |
| p-n-heptaoxyaniline* | 1-(p-n-heptaoxyphenyl)-5-(phenyl)biguanide |
| m-n-oxtaoxyaniline | 1-(m-n-octaoxyphenyl)-5-(phenyl)biguanide |
| o-n-octaoxyaniline | 1-(o-n-octaoxyphenyl)-5-(phenyl)biguanide |
| p-sec-octaoxyaniline | 1-(p-secoctaoxyphenyl)-5-(phenyl)biguanide |
| p-n-nonaoxyaniline* | 1-(p-n-nonaoxyphenyl)-5-(phenyl)biguanide |
| p-n-decaoxyaniline* | 1-(p-n-decaoxyphenyl)-5-(phenyl)biguanide |
| p-n-undecaoxyaniline | 1-(p-n-undecaoxyphenyl)-5-(phenyl)biguanide |
| p-n-dodecaoxyaniline* | 1-(p-n-dodecaoxyphenyl)-5-(phenyl)biguanide |
| p-n-tetradecaoxyaniline | 1-(p-n-tetradecaoxyphenyl)-5-(phenyl)biguanide |

*Commercially available; from Frinton Laboratories (Vineland, NJ) the remaining alkoxyanilines are made by alkoxylation of the corresponding hydroxyacetanilide with the desired alkyl halide.

EXAMPLE 3

Foliar Fungicidal Tests

For these tests, a suspension of the active ingredient at various concentrations is prepared in a mixture of acetone, water and surfactant, the latter being maintained at a constant level at all concentrations. The suspension is made from a standard solution of Triton X-155 (Rohm and Haas Co.) surfactant (1000 ppm) in acetone which is used to dissolve the active compound. The concentrated standard solution then is further diluted with water (1:9) to obtain a diluted stock solution which is a mixture of 10% acetone and 100 ppm of the surfactant in water. This diluted stock solution is used for further dilution of the dissolved compound solution for testing at various concentrations of active material. Thereby a constant ratio of surfactant is maintained at all compound concentration levels used in the tests.

A. Rice Spots

The compound of Example 1 was tested on rice leaf spot fungus as follows: Young Star Bonnet rice plants, about 2 weeks old, were grown in 2.5 inch clay pots, and, while rotating the pots, were sprayed with test liquid suspensions as prepared above. After the spray deposit dried, the plants were atomized with a colloidal suspension of the causative pathogen and placed in a moist chamber at 75° F. for 24 hours to facilitate infection. After discrete lesions appeared in the unprotected controls (2 days), the infection was rated on a scale of 0 (no reduction) to 10 (complete elimination of infection) versus the commercial standard Daconil, whose active ingredient is chlorothalonil.

| Rice Spot Fungitoxicity Ratings | | |
| --- | --- | --- |
| Conc. ppm | Compound of Ex. 1 | Daconil |
| 260 | 10 | 9 |
| 130 | 9 | 10 |
| 65 | 8½ | 10 |
| 33 | 8½ | 10 |

B. Bean Rust

The compound of Example 1 was tested on bean rust as follows: Pinto beans grown in 2.5 inch clay pots for 9 to 12 days were sprayed with test liquid suspensions while the plants were rotating on a turntable. About 100 ml. of each suspension was sprayed on the plants. After the spray deposit dried the plants were atomized with a colloidal suspension of the causative pathogen, and placed in a moist chamber at 70° F. for 24 hours. After 7 to 9 days, the severity of the pustule formation was rated on a scale of 0 (no reduction) to 10 (complete elimination of infection). The results were compared with the commercial fungicide Vitavax, whose active ingredient is carboxin.

| Bean Rust Fungitoxicity Ratings | | |
| --- | --- | --- |
| Conc. ppm | Compound of Ex. 1 | Vitavax |
| 260 | 10 | 10 |
| 130 | 9 | 10 |
| 65 | 8 | 10 |
| 33 | 8 | 7½ |
| 16 | 6 | 5 |
| 8 | 8 | 3 |

C. Apple Scab (Venturia inaequalis)

Protective ratings for control of fungi which cause apple scab were established on young apple trees grown in 7-inch clay pots. The trees were treated with the test formulation, which was prepared in diluting an emulifiable concentrate with water to the desired spray concentration. The formulation was applied by spraying the apple trees to drench. The trees were then subjected to the procedure of fungal infection of the leaves with apple scab spores under simulated rainfall conditions over a three-week period. The leaves then were examined. The amount of control was expressed on a scale of 0 to 10; where 10 is complete control (no infection) and 0 is no control, as shown by the unsprayed trees; the results were compared against the accepted commercial standard Benlate, whose active ingredient is benomyl.

| Apple Scab Fungitoxicity Ratings | | | |
| --- | --- | --- | --- |
| | Test No. | | |
| Compound-Conc. ppm | A | B | C |
| Ex. 1 - 226 ppm | 9 | 7 | 7 |
| Benlate - 226 ppm | 7 | 5 | 3 |

While the invention has been described with particular reference to certain embodiments thereof, it will be understood that changes and modifications may be made which are within the skill of the art. Therefore it is intended to be bound by the appended claims only.

What is claimed is:

1. A method for controlling the fungi on living plants comprising: contacting said fungi with a fungicidally effective amount of a compound having the formula:

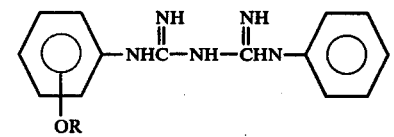

where R is alkyl, linear or branched, having from 1–14 carbon atoms, or acid addition salts thereof.

2. A method according to claim 1 wherein R is alkyl having 7–12 carbon atoms.

3. A method according to claim 1 wherein said compound is 1-(p-n-octaoxyphenyl)-5-(phenyl)biguanide.

4. A method according to claim 1 wherein said compound is applied in the form of a solution, suspension, emulsion, wettable powder or dust containing from 20 ppm to 5600 ppm of said compound.

5. A method according to claim 1 wherein the plants are fruit trees.

6. A method according to claim 1 wherein the fungi are those which cause apple scab.

7. A method according to claim 6 in which said compound is 1-(p-n-octaoxyphenyl)-5-(phenyl) biguanide.

* * * * *